United States Patent
Sigwanz et al.

(10) Patent No.: US 10,499,169 B2
(45) Date of Patent: Dec. 3, 2019

(54) AUTOMATICALLY DETERMINED USER EXPERIENCE VALUE FOR HEARING AID FITTING

(71) Applicant: Sonova AG, Staefa (CH)

(72) Inventors: Ullrich Sigwanz, Hombrechtikon (CH); Volker Kuehnel, Maennedorf (CH); Solange Anderson, Jona (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 15/900,830

(22) Filed: Feb. 21, 2018

(65) Prior Publication Data

US 2018/0242090 A1    Aug. 23, 2018

(30) Foreign Application Priority Data

Feb. 22, 2017    (EP) ...................... 17157347

(51) Int. Cl.
*H04R 25/00*    (2006.01)
*A61N 1/36*    (2006.01)
*G16H 40/63*    (2018.01)

(52) U.S. Cl.
CPC ......... *H04R 25/70* (2013.01); *A61N 1/36039* (2017.08); *G16H 40/63* (2018.01);
(Continued)

(58) Field of Classification Search
CPC .. H04R 25/70; H04R 25/505; H04R 2225/39; H04R 2225/55; H04R 2460/05; H04R 1/36039; G16H 40/63
See application file for complete search history.

(56) References Cited

U.S. PATENT DOCUMENTS 4,972,487 A    11/1990    Mangold et al.
5,794,201 A    8/1998    Nejime et al.
(Continued)

FOREIGN PATENT DOCUMENTS

EP    0335542 A2    10/1989
EP    1206163 A1    5/2002
(Continued)

OTHER PUBLICATIONS

European Patent Office, extended European Search Report, EP Patent Application 17157247.0, dated Jul. 14, 2017, 9 pages.

*Primary Examiner* — Joshua Kaufman (57) ABSTRACT

A method for adjusting a hearing device comprising: providing a user profile (42) of the user comprising actual user information (44) and a fitting history (47) stored in a database (34) of a fitting system (32), wherein the fitting history comprises fitting information (46, 46', 46") of at least one previous fitting session, in which previous fitting session the hearing device (10) or a different hearing device was adjusted for the user; determining a user experience value (54) of the user, wherein the user experience value (54) depends on the actual user information (44) and the fitting history (47); determining sound processing parameters (30) for the hearing device (10) based on the user experience value (54); and applying the determined sound processing parameters (30) in the hearing device (10), such that the hearing device (10) is adapted for generating optimized sound signals based on the applied sound processing parameters (30).

11 Claims, 2 Drawing Sheets

(52) U.S. Cl.
CPC .......... *H04R 25/505* (2013.01); *H04R 25/554* (2013.01); *H04R 2225/39* (2013.01); *H04R 2225/55* (2013.01); *H04R 2460/05* (2013.01); *H04R 2460/11* (2013.01)

(56) References Cited

U.S. PATENT DOCUMENTS

| | | |
|---|---|---|
| 6,118,877 A | 9/2000 | Lindemann et al. |
| 2002/0007158 A1 | 1/2002 | Burbank et al. |
| 2003/0013810 A1 | 1/2003 | Kaifu et al. |
| 2004/0006694 A1 | 1/2004 | Heelan et al. |
| 2004/0190739 A1* | 9/2004 | Bachler ................ H04R 25/305 381/314 |
| 2008/0187146 A1* | 8/2008 | Yanz ...................... H04R 25/70 381/60 |
| 2010/0020992 A1* | 1/2010 | Flynn .................... H04R 25/70 381/314 |
| 2011/0258839 A1 | 10/2011 | Probst |
| 2012/0018316 A1 | 1/2012 | Salinas-Barrera et al. |

FOREIGN PATENT DOCUMENTS

| | | |
|---|---|---|
| EP | 2368374 A1 | 9/2011 |
| WO | 200041440 A | 7/2000 |
| WO | 2009068696 | 6/2009 |

\* cited by examiner

AUTOMATICALLY DETERMINED USER EXPERIENCE VALUE FOR HEARING AID FITTING

CROSS-RELATED APPLICATION

The application claims priority to European Patent Application No. 17157347.0, titled "Automatically Determined User Experience Value For Hearing Device Fitting," filed on Feb. 22, 2017, which is incorporated herein for its entirety.

TECHNICAL FIELD

The disclosed technology relates to the field of hearing devices. In particular, the disclosed technology relates to a method and fitting system to fit a hearing device.

BACKGROUND

Hearing devices are usually fit in a fitting session. During a fitting session, a hearing care professional adjusts a hearing device to the needs of a user. For example, the hearing care professional can adjust the gain of a hearing device, a mode of a hearing device, or other parameters of the hearing device during a fitting session. A first fitting session refers to the first time a hearing care professional attempts to fit a hearing device, but it may not be the first time a user has been fit for a hearing device.

The effectiveness of a fitting session can depend on the user's experience with hearing devices. For example, if a user has previously used a hearing device, he or she may be more likely to identify when a proposed fit is more or less effective. In contrast, if a user has never worn a hearing device before, he or she may be less likely to determine if a fit is comfortable because he or she is not experienced with the fitting process.

Hearing care professionals often guess an "initial fit" for a user based on a user's experience level and the hearing care professional's prior knowledge. If a hearing care professional guesses a setting that is far from a preferred setting during an initial fit, the user may experience discomfort early on, which leads to an unsatisfactory fitting. Further, an improperly fit hearing device can even cause the user to abandon hearing devices. Accordingly, there exists a need to overcome these shortcomings and improve the fitting of a hearing device fitting.

SUMMARY

The disclosed technology relates to fitting a hearing device. In some implementations, the disclosed technology relates to an initial or first fitting for a hearing device for a user. An initial fitting is a meeting (virtual or in-person) between a hearing care professional and a user to program a hearing device or adjust a hearing device for user. The disclosed technology executes an algorithm to fit a user to his or her new hearing device based on user experience values. The user experience values are information related to a user's history (e.g., fitting history), user characteristics (e.g., age, race, ear canal size, experience with hearing devices), or user preferences (e.g., prefers streaming or prefers to hear own voice as natural as possible).

A hearing device is a device that is adapted or configured to worn by a user at least partially in or on the ear. A hearing device may be a cochlear implant device with parts implanted inside the head. A new hearing device is a hearing device that has not been used by the user before. A previously used hearing device is a device that has been used and fit for the user.

The hearing device can be adapted for processing sound signals based on sound processing parameters stored in the hearing device such that hearing deficiencies of a user of the hearing device are compensated. The sound signals may be generated by a microphone of the hearing device and/or may be received via another input of the hearing device such as a T-coil or other interface, like a radio receiver. The sound processing parameters, which may be stored in a memory of the hearing device, may be parameters for a frequency dependent and level dependent amplifying of sound signals also referred to as "gain model" or "gain" of the hearing device and/or may encode how the sound signal is converted into a signal provided to the hearing sense of the user. Parameters may also related to compression or decompression of frequencies for hearing.

In some implementations, the disclosed technology includes a method for fitting a hearing device, the method comprising: providing a user profile of the user comprising actual user information and a fitting history stored in a database of a fitting system, wherein the fitting history comprises fitting information of at least one previous fitting session in which previous fitting session the hearing device or a different hearing device was adjusted for the user. The database may comprise the user profiles of a plurality of users. It may be that several fitting devices of the fitting system, which fitting devices are used by hearing care professionals, are connected to one central database storing the user profiles. Furthermore, every user profile may store a fitting history, such as a history of the fitting process of the user, e.g., fitting sessions of the user for previously fitted hearing devices.

A user profile may be identified by a user identification and may comprise further information about the user and/or the one or more hearing devices the user wears and/or has worn and the fitting process of these hearing devices to the user. The user identification may be the user's name, the user's previous hearing device, a user's medication record, client or contact number, phone number, or other personal information to identify a user. In some implementations, a hearing care professional can identify the user based on meeting the user and receiving personal information about the user. In other implementations, the user identification information can be received electronically (e.g., email, from a previous hearing device, or electronic survey).

The user profile may be a data structure stored in a database provided by a server device or the fitting device itself. The user profile include can include medical information, user history information, and other data related to the user's record or hearing. For example, the fitting device may be interconnected via a data communication network with the server device. It has to be noted that the server device need not be a single device but also may be provided by a system of devices, for example, a cloud computing facility. The fitting device may be a personal computer (PC), tablet, mobile device, or other computing device located at the site of the hearing device professional.

Fitting session information may be data stored in the database during a fitting of the hearing device. For example, a fitting session information may comprise the time (e.g., a date and time stamp), when the user has visited the hearing care professional, which hearing device was fitted at that time, an audiogram of the user at that time and/or the fitting parameters generated at that time. The fitting session information may also comprise logging data, which may be read from a memory of the hearing device. The logging data may comprise information such as wearing time of the hearing device during a period of time before the fitting session, or activation time for different programs or features of the hearing device.

In some implementations, the disclosed technology includes a method comprising: determining a user experience value of the user, wherein the user experience value depends on the actual user information and the fitting history. The user experience value may be a numerical value, for example an integer number. For example, a software implementing the method may look for the oldest fitting session and may determine the time difference from an actual time to the time of the fitting session. This time may be the time of generation of the user profile or may be the time at which the user previously attended a fitting session. For example, the user experience may be the time difference divided by a constant factor and/or may be determined with a function applied to the time difference.

The user experience value not only may depend on the time of the previous fitting session, but also on other information stored in the user profile. In general, the user experience value may be determined automatically from the information already stored in the user profile. In general, the information about the user that is stored in the database of the fitting system is used for determining the user experience value that may be seen as an objective quantity independent of the hearing care professional. For example, the user experience value may be automatically determined, when a new fitting session is started.

A user experience value can also be determined from other factors in the user profile. In some implementations, a user experience value can be determined from streaming information. For example, a user experience value can be based on a frequency or number of devices that used to stream information. A user may frequently stream (e.g., every day) music from his or her mobile device. Additionally, a user may not stream and just use the traditional hearing device functions such as amplification. In some implementations, a user experience value can be in a range from 1 to 10, where 1 means no streaming and 10 means constant or extremely frequent streaming. The disclosed technology can use this The method further comprises: determining sound processing parameters for the new hearing device based on the user experience value; and applying the determined sound processing parameters in the hearing device, such that the hearing device is adapted for generating optimized sound signals based on the applied sound processing parameters. In some implementations, the disclosed technology can use one, two, three, or more user experience values to adjust parameters in the hearing device. In some implementations, the method includes "computing", where computing generally means modifying sound processing parameters for the hearing device based on the user experience values.

Several example computations and algorithms are disclosed herein, but in general, the user experience values are multiplied, divided, added, or subtracted from sound processing parameters to adjust a fitting for a hearing device. For example, if a user experience value relates to a user being a new user (e.g., never worn a hearing device before), the user experience value can be $4/5$ and this value can be multiplied by the amplification factor of the hearing device such that the amplification of the hearing device is reduced by $1/5$ compared to a standard fit from the manufacturer. As another example, a user experience value associated with a user being new to hearing aids can cause a vent to stay open or open more than normal because new users prefer to have more ambient sound (as compared to a closed vent that reduces ambient sound).

The sound processing parameters may encode an adjusting a gain model and/or a mixing of sound signals from more than one sound source, such as mixing of sound signals picked up by microphones and/or sound signals picked up through a wired or wireless connection. Sound processing parameters may also control the directivity of the microphone system also referred to as beamforming. They may further control sound cleaning features such as noise cancelling. They may control shifting a frequency range to another range. They may control feedback cancelling algorithms. The sound processing parameters may be defined as technical parameters or control parameters of the hearing device, which may directly control the behavior of the hearing device. A set of sound processing parameters may be assigned to a program. The hearing device may comprise one or more programs. A program may be manually selected by the user or be automatically selected based on a classification of an actual acoustic environment.

For example, the fitting database may comprise profiles for sound processing parameters for different user experience values. A profile may comprise a fitting formula for providing a gain model in dependence of an audiogram, which describes the hearing loss of a user. When a user experience value has been determined, the corresponding profile may be loaded into the fitting device. The profile may optionally be edited and/or fine-tuned by the hearing care professional. After that, the profile may be applied to the hearing device. Applying comprises generating one or more sets of parameters and loading them into the hearing device.

In some implementations, the actual user information comprises an actual time and the fitting information comprises a time when the at least one previous fitting session was carried out and the fitting history comprises a time which has passed since the time of the at least one previous fitting session stored in the user profile.

In some implementations, an initial user experience value is determined based on the time, which has passed since the time of the at least one previous fitting session. After that the initial user experience value may be modified based on further information stored in the user profile. In other words, the initial user experience value, which may be seen as a first estimate, may be modified with one or more modifiers, which are determined from user information (e.g., age).

In some implementations, the fitting history comprises further information stored in the user profile. For example, the fitting history comprises diagnostic information (such as an audiogram) of previous fitting sessions and/or hearing device information (such as the type of the hearing device) of previously worn hearing devices.

It has to be noted that the modifiers for the experience value also may be based on the fitting history. When specific values encoded in the user profile changes of time, such as a hearing ability (that may be encoded in audiograms over time), this may result in a modifier reducing the initial user experience value. The modifiers may be numerical values, which are added and/or subtracted from the initial user experience value. Also, the modifiers may be averaged before being added to the initial user experience value.

In some implementations, the user experience value comprises at least three different values for a first time user, a short term user, and a long term user. When the user experience value may be only three different values, only three profiles for sound processing parameters may have to be stored. The user experience values may be 1, 2, and 3 for first time user, short term user and long term user, respectively.

For example, the user experience value may be set to "first time user", when the passed time is shorter than a first time user period. As an example, the first time user period may be 4 weeks. The user experience value may be set to "long term user", when the passed time is longer than a long term user period. As an example, the long term user period may be 6 months. Furthermore, the user experience value may be set to "short term user", when the passed time is between the first time user period and the long term user period.

As another example, a user experience value may adjust depending on age. For example, younger users generally have less hearing loss and may want less amplification and less occlusion from a vent. Young users can be assigned a user experience value of 1. Older users may prefer for more amplification and more occlusion, as such a user experience value for older users can be 2 or 3.

Based on this user experience value, the fitting software can increase or decrease fitting parameters in the hearing device. For example, the fitting software can send a control signal to the hearing device to multiply an amplification factor or gains by ½ for users with a user experience value of 1 and multiple the amplification factor or gain by 2 for users with a user experience value of 2 or 3. Similarly, a user experience value can be associated with modifying a vent: a high value opens the vent (less occlusion more ambient noise) or low value for closing the vent (increase occlusion to reduce ambient noise and focus on sounds generated in ear canal by receiver). The amount of a occlusion (e.g., open, closed, or partially open/closed) can be computed as an occlusion parameter, where an occlusion parameter is a value that determines how open a vent should be. For example, an occlusion parameter of 0 can mean a vent is completely closed, an occlusion parameter of 5 can be mean a vent is half open, and an occlusion parameter for 10 can mean a vent is completely open. In such an example, values of 2, 3, 4, 6, 7, 8, or 9 can be values that are partially open. The occlusion parameter can also vary depending on the listening scenario. For example, the occlusion parameter can be associated with streaming, where the occlusion parameter is 0 (closed) when streaming or it can be 10 (open) when streaming if a user prefers to hearing ambient noise when streaming.

In some implementations, the user profile comprises hearing device wearing times, which wearing time indicate, when a user has worn a hearing device since the time of the earliest fitting session. The user experience value may be reduced, when the hearing device wearing times indicate a time period, in which the user has not worn a hearing device. The user profile may store time information that may be used for determining a modifier for the initial user experience value.

Reducing of the user experience value may mean that the user experience value is set to a value indicating that the user has less experience. When the user experience value is a numerical value, which is becoming higher, when the user has more experience, the user experience value may be reduced by subtraction. However, it may be that in the opposite case, a numerical value used for the user experience may become higher, when being reduced.

The user experience value only may be reduced, when the time period is longer than a threshold time period, such as 6 months. For example, in this case, a modifier of −1 may be generated.

In some implementations, the user experience value may be further reduced, when the time period, in which the user has not worn a hearing device, is a multiple of a threshold time period. For example, the threshold time period may be between 4 months and 1 year. For example, every 6 months, the user has not worn a hearing device since the time of the previous fitting session, a modifier of −1 may be generated.

In some implementations, the actual user information comprises actual diagnostic information of the user and the fitting history comprises at least one diagnostic information recorded in a previous fitting session.

In this case, the user experience value may be adjusted based on the diagnostic information. Diagnostic information may be any information regarding the hearing abilities of the user.

According to an embodiment the actual user information comprises an actual audiogram and the diagnostic data comprises a previous audiogram. For example, besides audiograms, the diagnostic information also may contain information about tinnitus.

It may be that a user with an only small hearing loss may receive a higher user experience value than a user with a severe hearing loss. For example, for a user with a hearing loss less than a threshold value (which may be provided as a pure tone average value), the user experience value may be increased.

In some implementations, the user experience value is reduced, when comparing the actual audiogram with a previous audiogram indicates a difference of the hearing abilities of the user by more than a hearing loss threshold value. The difference may be understood as an absolute value. A PTA (pure tone average) may be determined for the actual audiogram and the previous audiogram and a difference of these PTA values may be used for quantifying a hearing loss difference. Pure-tone average (PTA) may be the average of hearing sensitivity at 500, 1000 and 2000 Hz.

While in many cases the hearing loss of a user increases, it is also possible, that an improvement of the hearing capabilities occurs, for example as a result of an operation. Also in this enjoyable case the user experience value may be reduced.

In some implementations, the user experience value is reduced, when the loss by more of the threshold value was determined for a time period of fixed length. For example, a difference of 15 dB PTA (pure tone average) during the last 6 months may result in reducing the user experience value. In this case, a modifier of −1 may be generated.

In some implementations, the user experience value is reduced, when the loss by more of the threshold value is determined for a time period since the last fitting session. Also, big differences of the hearing losses may result in a modifier reducing the user experience value. For example, a reduction of the PTA of 15 dB since the last fitting session may result in a modifier of −1.

In some implementations, the actual user information comprises information about a new hearing device to be fitted and the fitting history comprises information about a previously worn hearing device. The hearing device information may comprise a type number and/or serial number of the hearing device, a list of features of the hearing device, and/or configuration data of the hearing device, such as the actual sound processing parameters currently stored in the hearing device. In some implementations, the user experience value is adjusted based on the hearing device information. In particular, when the type of hearing device and/or its amplification class changes, this may result in a modifier for the user experience value.

In some implementations, the user experience value is reduced, when the new hearing device has a different maximal amplification factor than the previously worn hearing device. For example, hearing devices may be classified into three classes: small amplification, medium amplification and high amplification. When a user changes from small to medium or from medium to high amplification, this may result in a modifier of −1. When the user changes from small to high amplification, this may result in a modifier of −2.

In some implementations, the user experience value is reduced, when the new hearing device and the previously worn hearing device are of a different type. For example, hearing devices may be differentiated, whether they are open hearing devices or closed hearing devices, e.g., whether the hearing device is occluding the ear channel significantly or not. Also hearing devices are from different manufacturers, e.g., a change of manufacturer may result in a reduction of the user experience value. Also in these cases, a modifier of −1 may be generated.

In addition to determining whether a hearing device is open or closed, the disclosed technology can determine how to adjust an adjustable vent in a hearing device. For example, some hearing devices have adjustable vents—vents that can open or close partially or completely. The vents can be controlled magnetically, mechanically, or electrically. The disclosed technology can determine that a prior hearing device generally had an open vent for most settings or a closed vent for a few settings. The disclosed technology can then cause a user experience value to change such that the vent is adjusted. For example, if the user experience value is increased or decreased, it can result in a vent size changing (e.g., opening or closing).

In some implementations, a user experience value is based size of a user's ear canal, which would have impact on the choice of receivers as such. Bigger ear canals will allow bigger (stronger receivers) with higher gain (especially low-frequency-gain), which could then compensate for the loss in low frequencies that come with more open couplings. In some implementations, a user experience value is based on streaming (or alterative input) sources, which would require stronger receivers and/or more closed coupling for providing a reasonable sound quality for these input sources.

A further aspect of the invention relates to a fitting system for adjusting a hearing device, the fitting system being adapted for automatically carrying out the method as described in the above and in the below. The fitting system may comprise one or more fitting devices and a user profile database that may be provided in a further server device. For example, the one or more fitting devices may be connected to the user profile database via a data communication network such as the Internet or an intranet.

Additionally, the disclosed technology solves at least one technical problem related to the computer environment and hearing devices. Different hearing devices have different software, hardware, and store data in different formats. As a result, hearing devices lack a universal value or method for carrying hearing device settings from one device to another device. Additionally, each hearing device can have a proprietary fitting software associated with it and this fitting software can be related to an audiogram. Having one universal value that can adjust settings for a hearing device, regardless of model or manufacture, and based on user's experience, enables hearing care professionals to automatically fit a hearing device for a user without re-programming or taking another audiogram. Additionally, hearing devices lack significant processing power and memory to automatically adjust or update fitting software locally, and thus using a user experience value can inform the hearing device how to adjust accordingly without performing significant computation or using a lot of memory.

It has to be understood that features of the method as described in the above and in the following may be features of the computer program, the computer-readable medium and the fitting system as described in the above and in the following, and vice versa. These and other aspects of the invention will be apparent from and elucidated with reference to the embodiments described hereinafter.

BRIEF DESCRIPTION OF THE DRAWINGS

The reference symbols used in the drawings, and their meanings, are listed in summary form in the list of reference symbols. In principle, identical parts are provided with the same reference symbols in the figures.

DETAILED DESCRIPTION

Figure 1:
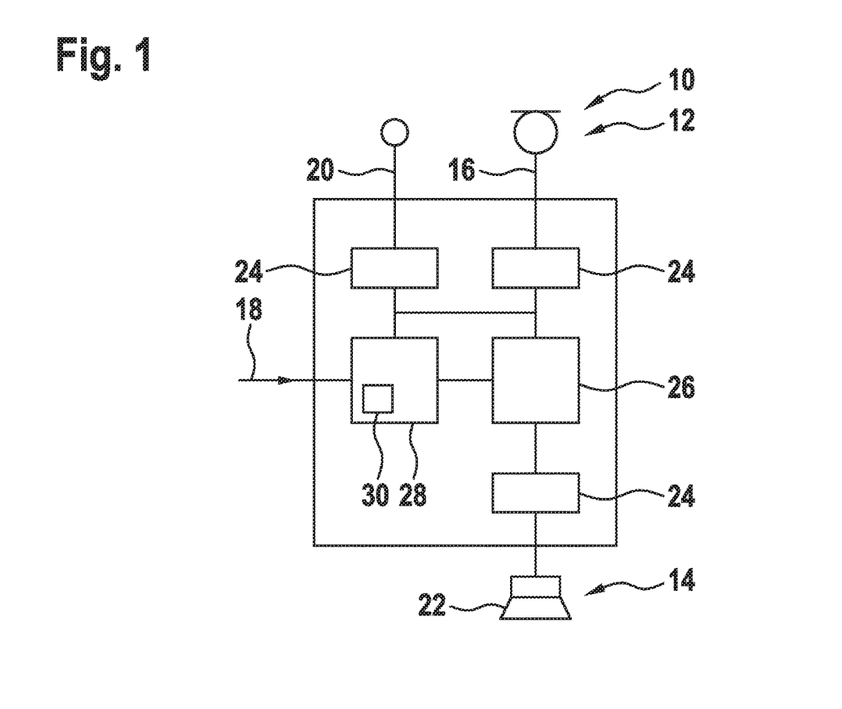
FIG. 1 schematically shows a hearing device adjusted by a fitting system in accordance with some implementations of the disclosed technology.

FIG. 1 schematically shows a hearing device 10. A hearing device 10 can be a device that may be put at least partially into an ear of a user to at least partially compensate an auditory defect of the user. In general, a hearing device 10 may be near the ear, at least partially in the ear channel and/or carried on the ear. It has to be noted that a hearing device 10 may comprise two separate devices for each ear of the user (e.g., hearing aids, in-the-ear hearing aids, in-the-canal hearing aids, behind-the-ear hearing aids). It also may be possible that the hearing device 10 comprises a cochlear implant, which may be partially or completely inside the head of the user.

The hearing device 10 comprises an input 12 for receiving sound data and an output 14 for generating signals such as audio signals for the user. The input 12 may comprise a microphone 16 and a sender/receiver 18 for control signals, which may be transferred via infrared, electromagnetic waves and/or cable. A further receiver for electromagnetic waves also may be a so-called T-coil or telecoil 20. The output 14 may comprise a loudspeaker 22 in the ear channel or a stimulation device inside the cochlear.

An analog signal from one if the inputs may be transformed by a corresponding transducer 24 into a digital signal. For example, the microphone 16 and/or the T-coil 20 may generate analog sound signals, which may be then transduced into digital sound signals or sound data that may be processed by an amplifier 26. The amplifier transforms input sound data into optimized output sound data for the output 14. The amplifier 26 usually comprises a processor (or at least a digital electronic circuit), which may perform the transformation of the sound data.

The hearing device 10 furthermore comprises a controller 28 with a memory and a processor, which controls the operation of the amplifier 26. It may be possible that the amplifier 26 is a module of the controller 28. In the memory of the controller 28, sound processing parameters 30 are stored, which parametrize the control of the amplifier 26.

For example, the sound processing parameters 30 may encode an adjusting a frequency dependent amplifying of sound data in the amplifier 26 and/or a mixing of sound data from more than one source 16, 20. In general, the sound processing parameters also may control a processing of sound data inside the hearing device 10.

Via the receiver 18, the controller 28 may receive control signals. For example, the controller 28 may receive modified sound processing parameters 30. Furthermore, the controller 28 may receive commands for modifying the sound processing parameters and/or for switching into another operation mode.

Figure 2:
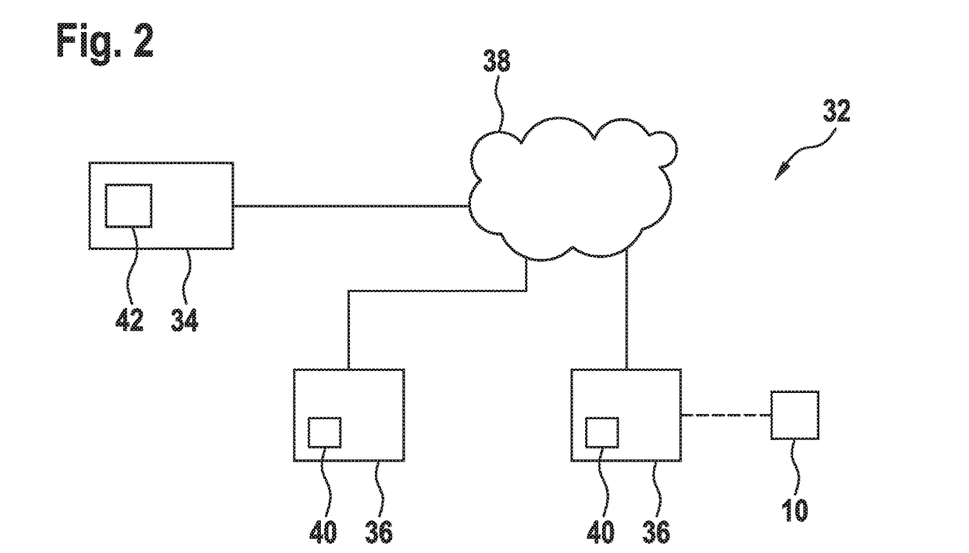
FIG. 2 schematically shows a fitting system in accordance with some implementations of the disclosed technology.

FIG. 2 shows a fitting system 32 for fitting the hearing device 10. The fitting system 32 may comprise a central database 34 and one or more fitting devices 36 that may be connected with the database 34 via a data communication network 38. Alternatively, the database 34 may be provided in the fitting device 36.

In some implementations, the database stores hearing information for a user in a common database, where common means that the results of the hearing test can be used by a fitter from many manufactures (e.g., universally readable data). For example, the database 34 can be physically coupled to a Noah System 4™, which is maintained by the Hearing Instrument Manufacturers' Software Association (HIMSA). By storing data in a common format even though it may have come from a propriety database and fitting software, the database provides user specific fitting information that can be applied to any device for any fitting session.

Each fitting device 36 may be a computer, PC, a tablet, computer situated in a shop/office of a hearing care specialist, or a mobile device (e.g., tablet, laptop, or mobile phone). In the fitting device 36, a fitting application 40 is executed that may be used for fitting a hearing device 10. When the user is in the shop/office of the hearing device specialist, the hearing device specialist may use the fitting device 36 and/or the fitting application 40 for directly adjusting the hearing device 10 by modifying the sound processing parameters 30. For example, the fitting device 36 may be adapted for updating the sound processing parameters 30 in the hearing device 10 via a direct connection via the sender/receiver 18.

The fitting device 36 may be communicatively coupled with the database 34, for example via a data communication network 38. During the fitting at his store/office, the hearing care specialist may input information about the user of the hearing device, for example about his life situation (for example "retired", "assisted living", "age", "gender", "ethnicity"), into the fitting application 40, which will then send this information to the database 34, which will create a user profile 42 of the user. The life situation can be correlated to a life situation parameter, where the value of a parameter is such that it can be increased or decreased to cause the hearing device to match a life style of the user (e.g., more amplification for older or retired people, and less amplification for younger people). It also may be possible that other information gathered by the fitting device 36 and/or the fitting application, such as an audiogram of the user, may be sent and/or stored in the database 34 in the user profile 42. One database 34 interconnected with several fitting devices may have the advantage that the user may visit different stores/offices of different hearing care specialists, which, however, may access the same information from the user profile 42.

In some implementations, a hearing care professional and user may be located in remote locations and the fitting session can be carried out remotely. For example, a hearing care professional can host an online fitting session through a cloud service, where the user can hear care professionals communicate via the Internet.

Figure 3:
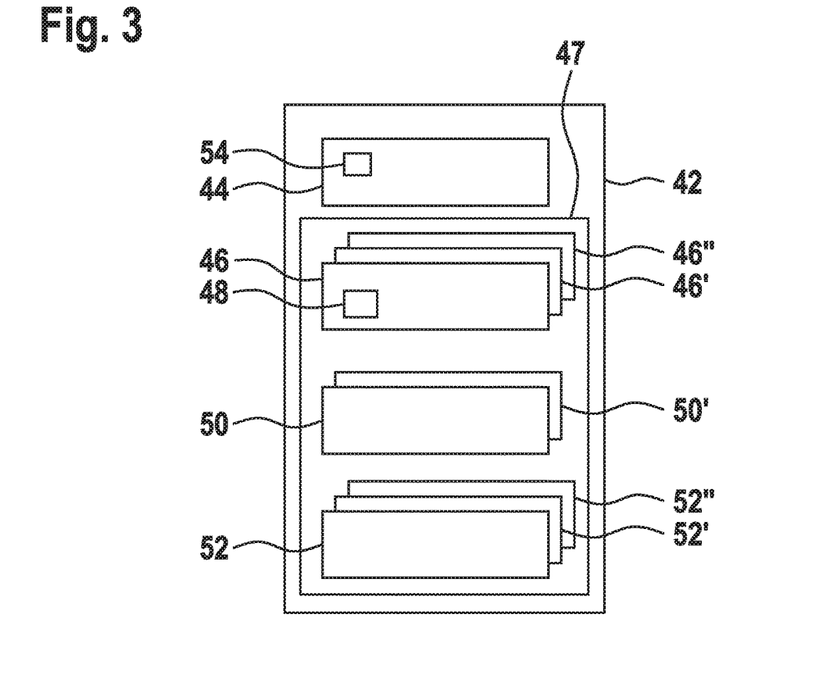
FIG. 3 shows a user profile used by the fitting system of FIG. 2.

FIG. 3 shows a user profile 42 in detail. The database 34 may store user profiles 42 of many users. The user profile 42 contains actual user information 44, such as a numerical identifier, name and residence of the user, age, etc. This information may be input or updated into the fitting application 40, when the user visits a hearing care specialist. The user information also may comprise actual audiological data such as an audiogram or a preference (such as a gain model), a socio-ecological preference (such as one or more preferred sound environments such as cocktail party or concert with classical music, in which the user wishes to use the hearing device 10), and/or a usage preference (such as preferred accessories, device options of the hearing device 10).

Also, the user profile 42 contains a fitting history 47 the fitting history 47 comprises fitting information 46, 46', 46" about an actual fitting session and previously conducted fitting sessions when the user attends at the hearing care specialist. In a fitting session, a hearing care specialist may fit, e.g., adapt, a new or already worn hearing device 10 to the needs of the user. Furthermore, the hearing care specialist may record an audiogram of the user and/or may perform tests with the user.

The fitting session information 46 may contain a time 48 (the time typically comprises a date) of the fitting session. Further information that may be stored in the fitting history 47 may be divided into diagnostic information 50, 50' and/or hearing device information 52, 52', 52". For example, the diagnostic information 50, 50' may comprise audiograms recorded for the user. The hearing device information 52, 52', 52" may contain the types of hearing devices 10 used by the user over the time, the corresponding sound processing parameters 30 and/or the wear times of the hearing devices 10.

It has to be noted that histories of all of these information 44, 46, 46', 46", 50, 50,' 52, 52', 52" may exist, as indicated by the layered rectangles. There may be a fitting session information history 46, 46', 46", a diagnostic information history 50, 50' and/or a hearing device information history 52, 52', 52".

In particular, it may be possible to compare different audiograms over time and/or to determine times, when the user has worn a hearing 10 or not. Furthermore, it may be possible to determine, when a user has attended fitting sessions, and/or when he has visited a hearing care specialist for the first time.

The times or dates of consecutive fitting session times or dates for one type of hearing device 10, the number of fitting sessions per se, the time of the first fitting session in the database 34, the history of audiograms may provide valuable hints about the experience of the user with hearing devices 10 and/or their features.

A user experience value 54 may be stored in the user profile 42, for example in the actual user information 44, which indicates the above-mentioned experience of the user with hearing devices 10. The user experience value 54 may be used during a fitting session for selecting specific profiles for the sound processing parameters 30 and/or in general may help the hearing care specialist for fitting the hearing device 10.

The user experience value 54 may be stored in the fitting session information 46, 46', 46" together with the times of the fitting sessions. In such a way, it is possible to judge the progression of a user experience over time. In such a way, the progression of a plurality of users may be compared and/or optimal profiles for sound processing parameters may be derived based on these progressions.

Figure 4:
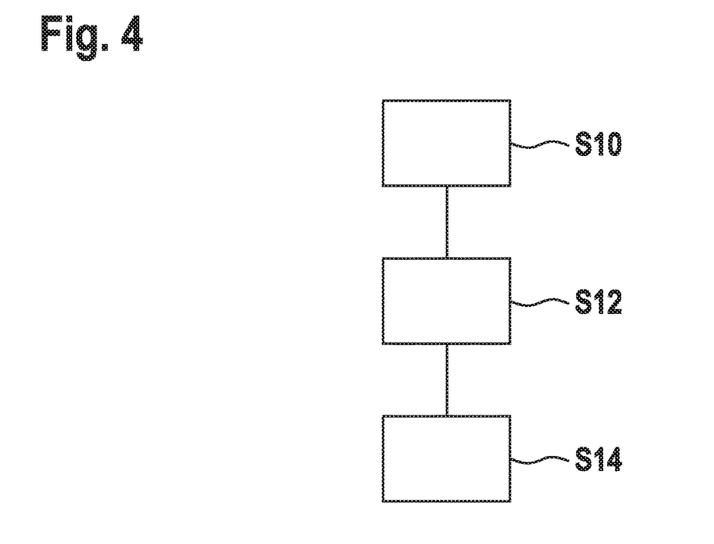
FIG. 4 shows a flow diagram for a method for adjusting a hearing device in accordance with some implementations of the disclosed technology.

FIG. 4 shows a method for automatically determining the user experience value 54 based on the above-mentioned information and for adjusting the hearing 10 based on the user experience value 54.

In step S10, a hearing care specialist starts a new fitting session with a user of a hearing device 10. The hearing care specialist starts the application 40 and, for example, inputs a name or other identifier of the user. The application 40 sends the corresponding data to the database 34, which provides the user profile 42 of the user 42. Furthermore, the fitting application 40 may advise the database 34 to generate a new fitting session.

In step S12, a user experience value 54 of the user based on the information 44, 46, 46', 46", 50, 50', 52, 52', 52" is generated. The user experience value 54 is generated automatically by the application 40, when a new fitting session with actual user information 44 is generated in the user profile 42. It also may be possible that the user experience value is generated on demand by the hearing care specialist and/or when data, on which the user experience value 54 is based, changes. For example, the user experience value 54 may be based on an actual audiogram of the user and may be updated, when the hearing care specialist has finished recording an audiogram of the user with the fitting application 40.

For so-called guest-fittings or holiday-fittings (which may refer to fitting sessions of users that are not present in the databases 34 yet), the application 40 may deny further access to a fitting workflow unless the hearing care professional has explicitly asked the user for her/his wearing experience and finally enters this user experience value manually into the fitting application 40. It also may be possible that the hearing care professional is forced to input the information needed for the calculation of the user experience value 54.

In an example, the user experience value 54 solely depends on a time which has passed since a time of an earliest fitting session stored in the user profile 42. For example, the database 34 may search for the earliest value of a fitting session time 48 and then may determine the user experience value 54 from a difference of this time to the actual time and/or date.

For example, the user experience value 54 may comprise at least three different values for a first time user, a short term user and a long term user. These three different values may be presented by 1, 2 and 3. A user may be a first time user, when the above-mentioned difference is less than 1 month. A user may be a short term user, when the difference is between 1 month and 6 months. Otherwise, the user may be a long term user. However, it also may be possible that the user experience value 54 is provided as a value in a range, for example as a value between 1 and 10.

The determination of the user experience value 54 solely based on a first fitting session time may be used for determining an initial user experience value 54, which is modified based on further information 50, 50', 52, 52', 52" stored in the user profile 42. From the further information, such as wearing times, hearing device types, audiograms, etc., modifiers may be determined, which may be added and/or subtracted from an initial user experience value 54.

For example, a hearing device type of a new manufacture may result in a modifier of −1. Also, a high difference of the hearing loss since the last fitting session may result in a modifier of −1.

These modifiers may be added directly to the user experience value 54. However, it is also possible that the modifiers are culminated in other ways. For example, a minimum and sum of the modifiers may be determined and the average of these two values may be added to the initial user experience value. For two modifiers of −1, this would result in $((-1)+(-2))/2=-1\frac{1}{2}$ as overall modifier.

In the following, several examples are provided, how the user experience value 54 may be modified based on additional information 46, 50, 52 stored in the user profile 42. It has to be noted that every example also may be seen as a modifier of an user experience value 54 that may be treated as above.

As indicated above, the user information 44 and/or the hearing device information 52 may store times and/or dates and/or time periods, in which a user has worn hearing devices 10 or not. The user experience value 54 may be reduced, when hearing device wearing times indicate a time period, in which the user has not worn a hearing device 10, for example for a time period of more than 6 months. Alternatively, the user experience value 54 may be further reduced, when the time period, in which the user has not worn a hearing device 10, is a multiple of a threshold time period, such as 6 months.

For example, a modifier for −1 may be generated, for every 6 months a user has not worn a hearing device since the time of the previous fitting session.

Also, audiograms stored in the diagnostic information 50 may be used for adjusting the user experience value 54. For example, the diagnostic information 50 may comprise an actual audiogram and at least one audiogram recorded in a previous fitting session. A comparison of the actual audiogram with a previous audiogram may indicate a hearing loss. Differences of the hearing losses about a threshold may reduce the user experience value 54 and/or may generate a modifier (such as −1). For example, from every audiogram, a pure tone average may be calculated and a difference of more than 15 dB may result in such a modifier.

Such comparisons between audiograms in a history of audiograms also may be applied to longer time periods. For example, the user experience value 54 may be reduced, when the hearing loss by more of the threshold value is determined for a time period of fixed length, for example for the last 6 months.

It also is possible that sudden differences of hearing losses by more than the threshold value result in a reduction of the user experience value 54 or a corresponding modifier. A sudden difference of hearing loss may be determined by comparing an actual audiogram with the last audiogram.

Not only diagnostic information 50 relating to the user but also hearing device information 52 relating to the hearing device 10 or a history of the hearing devices 10 worn by the user may be used for adjusting the user experience value 54.

A change of the manufacturer and/or the type of the hearing device may reduce the user experience value 54 and/or may result in a corresponding modifier.

For example, a maximal amplification factor of the actual hearing device 10 and the least worn hearing device may be determined from the hearing device information 52.

When the maximal amplification factors of the two hearing devices 10 differ strongly, for example belong to different classes, the user experience value 54 may be reduced or a corresponding modifier may be generated. For example, the hearing devices 10 may be classified into weak, medium and strong amplification. When the two hearing devices 10 are in two different classes, this may result in a modifier of −1. When one of the hearing devices 10 is in the weak class and the other one is in the strong class, then even a modifier of −2 may be generated.

In step S14, the hearing device is adjusted based on the user experience value 54. In general, the hearing care professional may adapt the current settings of the hearing device 10 to the new user experience value 54. This may be done in an automated or at least half-automated way.

Sound processing parameters 30 for the hearing device 10 may be determined based on the user experience value 54 by the application 40. For example, the application 40 may retrieve a profile of the sound processing parameters 30 for the type of hearing device 10 of the user from the database 34, which are provided for the determined user experience value 54.

It also may be possible that the application 40 adapts the actual sound processing parameters 30 of the hearing device 10 based on an algorithm. For example, a gain for a specific frequency may be adjusted to a higher value, when the user has moved to a higher experience value.

It has to be noted that the automatically generated sound processing parameters 30 may be modified by the hearing care specialist, to adapt them better to the need of the user.

In the end, the application 40 applies the determined sound processing parameters 30 in the hearing device 10. For example, the sound processing parameters 30 are sent to the hearing device 10 by the interface 18.

Here are some example tables for user experience values. In the tables, xS general means small or low power for the receiver, xM generally means medium power for the receiver, and xP generally means high power for the user. The following tables demonstrate how an appropriate acoustic coupling (e.g., receiver, ear piece, venting) is determined, based a user experience value related to fitting history, ear canal size, or streaming preferences. Also, a user experience value can related to an adaptive, steerable vent. An adjustable vent can be set according to the experience status of the client, e.g., reduce the vent size over time.

TABLE 1

First Time User and User Experience Values

| User | | First time Hearing Device User | | | |
|---|---|---|---|---|---|
| Ear Canal | | Small | | Regular & up | |
| Streaming | | No | Yes | No | Yes |
| Device 1 Hearing loss | Receiver | xS | xM | xM | xM |
| | Ear piece | Dome | Dome | Dome | Dome |
| | Venting | Open | Open | Open | Open |
| Device 2 Hearing loss | Receiver | xP | xP | xP | xP |
| | Ear piece | Dome | Dome | c-shell | c-shell |
| | Venting | Power dome | Power dome | Power dome | Power dome |
| Device 3 Hearing loss | Receiver | xS | xM | xS | xS |
| | Ear piece | Dome | Dome | Dome | Dome |
| | Venting | Open | Open | Open | Open |

TABLE 2

Experienced User and User Experience Values

| User | | Experienced Hearing Device User | | | |
|---|---|---|---|---|---|
| Ear Canal | | Small | | Regular & up | |
| Streaming | | No | Yes | No | Yes |
| Device 1 Hearing loss | Receiver | xM | xM | xP | xP |
| | Ear piece | Dome | Dome | Dome | Dome |
| | Venting | Closed | Closed | Closed | Closed |
| Device 2 Hearing loss | Receiver | xP | xP | xP | xP |
| | Ear piece | c-shell | c-shell | c-shell | c-shell |
| | Venting | pressure | pressure | pressure | pressure |
| Device 3 Hearing loss | Receiver | xM | xM | xM | xP |
| | Ear piece | Dome | Dome | Dome | Dome |
| | Venting | Closed | Closed | Closed | Closed |

TABLE 3

Experienced User and User Experience Values

| User | | Long term Hearing Device User | | | |
|---|---|---|---|---|---|
| Ear Canal | | Small | | Regular & up | |
| Streaming | | No | Yes | No | Yes |
| Device 1 Hearing loss | Receiver | xM | xM | xP | xP |
| | Ear piece | c-shell | c-shell | c-shell | c-shell |
| | Venting | 1.5 mm | 1.5 mm | 1.5 mm | 1.5 mm |
| Device 2 Hearing loss | Receiver | xP | xP | xP | xP |
| | Ear piece | c-shell | c-shell | c-shell | c-shell |
| | Venting | Pressure (partially open or partially closed) | pressure | pressure | pressure |
| Device 3 Hearing loss | Receiver | xS | xM | xS | xP |
| | Ear piece | Dome | Dome | Dome | Dome |
| | Venting | Closed | Closed | Closed | Closed |

In some implementations, the disclosed technology is a method stored on a computer-readable medium and the method is executed by a processor that causes a device to perform operations. The method can relate to a computer program for adjusting a hearing device, which, when being executed by the processor, is adapted to carry out the steps of the method as described in the above and in the following. The computer program may run in the fitting device. A computer-readable medium may be a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g., the Internet or an intranet, which allows downloading a program code. In general, the computer-readable medium can be a non-transitory or transitory medium excluding transitory signals.

Although the disclosed technology has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SYMBOLS

10 Hearing device
12 Input of hearing device
14 Output of hearing device
16 Microphone 18 Sender/receiver
20 T-coil
22 Loudspeaker
24 Transducer
26 Amplifier
28 Controller
30 Sound processing parameters
32 Fitting system
34 Database
36 Fitting device
38 Data communication network
40 Fitting application
42 User profile
44 User information
46 Fitting session information
47 Fitting history
48 Time of fitting session
50 Diagnostic information
52 Hearing device information
54 User experience value

We claim:

1. A computer-implemented method for fitting a new hearing device for a user, the method comprising:
receiving user identification information for fitting a new hearing device,
wherein the new hearing device has not been used by the user before;
determining, at a fitting station, a user profile based on the user identification information,
wherein the user profile is associated with a data structure stored in a database accessible via an internet, via an intranet, or at the fitting station,
wherein the user profile comprises a user experience value, and wherein the user experience value is based on three factors:
experience level of the user,
age of the user,
earliest fitting date for the user; and
computing, at the fitting station, fit settings for the new hearing device based on the user experience value, wherein computing includes determining sound processing parameters for the new hearing device and determining an occlusion parameter for the hearing device; and
transmitting the sound processing parameters and the occlusion parameter to the new hearing device.

2. The computer-implemented method of claim 1, wherein the earliest fitting date is associated with a time a previous fitting session was carried out, and wherein if the user has not been fitting before the earliest fitting date has a null value.

3. The computer-implemented method of claim 1, wherein the experience level of the user comprises values for a first time user, a short term user, and a long term user, wherein each value is different.

4. The computer-implemented method of claim 1, wherein the user profile includes a hearing device wearing time indicating when a user wore a hearing device since the time of the earliest fitting session.

5. The computer-implemented method of claim 1, wherein the user experience value is reduced when the new hearing device has a different maximal amplification factor than a previously worn hearing device for the user; and/or wherein the user experience value is reduced, when the new hearing device and the previously worn hearing device are of a different type.

6. A non-transitory computer-readable medium storing instructions that when executed by a processor cause a device to perform an operation, the operation to adjust a hearing device the operations comprising:
receiving user identification information for fitting a new hearing device,
wherein the new hearing device has not been used by the user before;
determining, at a fitting station, a user profile based on the user identification information,
wherein the user profile is associated with a data structure stored in a database accessible via an interne, via an intranet, or at the fitting station,
wherein the user profile comprises a user experience value, and wherein the user experience value is based on at least one of factors:
experience level of the user,
age of the user, and
earliest fitting date for the user;
computing, at the fitting station, fit settings for the new hearing device based on the user experience value, wherein computing includes determining sound processing parameters for the new hearing device and determining an occlusion parameter for the hearing device; and
transmitting the sound processing parameters and the occlusion parameter to the new hearing device.

7. The non-transitory computer-readable medium of claim 6, wherein the earliest fitting date is associated with a time a previous fitting session was carried out, and wherein if the user has not been fitting before the earliest fitting date has a null value.

8. The non-transitory computer-readable medium of claim 7, wherein the experience level of the user comprises values for a first time user, a short term user, and a long term user, wherein each value is different.

9. The non-transitory computer-readable medium of claim 7, wherein the user profile includes a hearing device wearing time indicating when a user wore a hearing device since the time of the earliest fitting session.

10. A computer-implemented method for fitting a hearing device for a user, the method comprising:
receiving user identification information for fitting a new hearing device,
wherein the new hearing device has not been used by the user before;
determining, at a fitting station, a user profile based on the user identification information,
wherein the user profile is associated with a data structure stored in a database accessible via an interne, via an intranet, or at the fitting station,
wherein the user profile comprises a user experience value, and wherein the user experience value is based on the three factors:
experience level of the user,
age of the user, and
earliest fitting date for the user;
computing, at the fitting station, a vent setting for the new hearing device based on the user experience value; and
transmitting the vent setting to the new hearing device, wherein the transmitted vent setting is configured to cause the hearing device to open or close a vent in accordance with the vent settings for the new hearing device.

11. The computer-implemented method of claim 10, wherein the vent setting is associated with the user streaming preference and the vent setting varies based on whether streaming is occurring.

* * * * *